United States Patent
Ling (10) Patent No.: US 12,415,181 B2
(45) Date of Patent: *Sep. 16, 2025

(54) BLOOD COLLECTION STRUCTURE AND WHOLE BLOOD AND FINGERTIP BLOOD TESTING DEVICE AND TESTING METHOD

(71) Applicant: ASSURE TECH. (HANGZHOU) CO., LTD., Zhejiang (CN)

(72) Inventor: Shisheng Ling, Hangzhou (CN)

(73) Assignee: ASSURE TECH. (HANGZHOU) CO., LTD., Hangzhou (CN)

( * ) Notice: Subject to any disclaimer, the term of this patent is extended or adjusted under 35 U.S.C. 154(b) by 1028 days.

This patent is subject to a terminal disclaimer.

(21) Appl. No.: 17/448,723

(22) Filed: Sep. 24, 2021

(65) Prior Publication Data

US 2022/0323950 A1    Oct. 13, 2022

Related U.S. Application Data

(63) Continuation of application No. PCT/CN2021/087100, filed on Apr. 14, 2021.

(30) Foreign Application Priority Data

Apr. 7, 2021   (CN) .......................... 202110376291.4

(51) Int. Cl.
B01L 3/00 (2006.01)
A61B 5/15 (2006.01)

(52) U.S. Cl.
CPC ........ B01L 3/502 (2013.01); A61B 5/150755 (2013.01); *B01L 2200/026* (2013.01);
(Continued)

(58) Field of Classification Search
None
See application file for complete search history.

(56) References Cited

U.S. PATENT DOCUMENTS 12,121,892 B2* 10/2024 Ling ................... A61B 10/0045
2004/0102717 A1* 5/2004 Qi ...................... A61B 5/15144
600/583

(Continued)

FOREIGN PATENT DOCUMENTS

CN     103983766 A    8/2014
CN     105842434 A    8/2016
(Continued)

OTHER PUBLICATIONS

International Search Report in PCT/CN2021/087100 mailed on Jan. 6, 2022, 8 pages.

*Primary Examiner* — Matthew Kremer
(74) *Attorney, Agent, or Firm* — METIS IP LLC (57) ABSTRACT

The present invention relates to a whole blood and fingertip blood testing device, including a blood collection structure and a testing chamber connected to and in fluid communication with the blood collection structure. The blood collection structure includes a collection rod, a capillary channel is arranged inside the collection rod, the bottom end of the capillary channel is located at the tail end of the collection rod, and the top end of the capillary channel is located in the middle of the capillary channel; and the collection rod is provided with a communicating hole connected to and communicated with the top end of the capillary channel. Moreover, the present invention also provides a method for collecting and testing a blood sample by using the testing device. Through the integrated structure of the blood collection structure, the testing chamber and the buffer chamber, the whole blood and fingertip blood testing device and method achieve functions of collecting, slowly releasing and testing the blood sample. The operation is easy, which reduces the difficulty of use by the operator. The number of times and time that the operator contacts the sample are effectively reduced, and the infectious possibility of the (Continued)

operator is reduced, so that the testing device is suitable for HIV testing, novel coronavirus testing, etc. The testing device and method have low requirements on the collected amount of the sample, and the collected amount is optimized from the milliliter level to the microliter level.

14 Claims, 8 Drawing Sheets

(52) U.S. Cl.
CPC . *B01L 2200/0689* (2013.01); *B01L 2200/082* (2013.01); *B01L 2200/16* (2013.01); *B01L 2300/025* (2013.01); *B01L 2300/044* (2013.01); *B01L 2300/047* (2013.01); *B01L 2300/0672* (2013.01); *B01L 2300/0838* (2013.01); *B01L 2400/0487* (2013.01)

(56) References Cited

U.S. PATENT DOCUMENTS

| | | | |
|---|---|---|---|
| 2005/0149088 A1* | 7/2005 | Fukuda | A61B 5/150503 |
| | | | 606/181 |
| 2005/0232813 A1 | 10/2005 | Karmali | |
| 2007/0213636 A1 | 9/2007 | Kuriger | |
| 2013/0216452 A1* | 8/2013 | Phan | G01N 1/38 |
| | | | 422/547 |
| 2017/0218436 A1* | 8/2017 | Azimi | B01L 3/50273 |

FOREIGN PATENT DOCUMENTS

| | | | | |
|---|---|---|---|---|
| CN | 108670272 A | 10/2018 | | |
| CN | 110477958 A | 11/2019 | | |
| CN | 210401424 U | 4/2020 | | |
| CN | 112034150 A | 12/2020 | | |
| WO | WO-9621483 A1 * | 7/1996 | | A61B 5/1405 |

* cited by examiner

BLOOD COLLECTION STRUCTURE AND WHOLE BLOOD AND FINGERTIP BLOOD TESTING DEVICE AND TESTING METHOD

CROSS-REFERENCE TO RELATED APPLICATIONS

This application claims priority to International Application No. PCT/CN2021/087100 filed on Apr. 14, 2021, which claims priority to Chinese Application No. 202110376291.4 filed on Apr. 7, 2021, the entire contents of each of which are hereby incorporated by reference.

TECHNICAL FIELD

The present invention relates to a blood collection structure and a whole blood and fingertip blood testing device and testing method, in particular to a blood collection structure and a whole blood and fingertip blood testing device and testing method, which are used for mixing a collected whole blood sample or fingertip blood sample with a buffer solution for testing.

BACKGROUND

The background art below is used to help readers understand the present invention, and cannot be regarded as the prior art.

The technology of using the immune binding reaction principle to test the presence of an analyte in a sample has been widely used in various fields. It can be used to test analytes in various biological samples (saliva, blood, urine, serum, sweat, etc.) to monitor diseases and human health conditions (early pregnancy, tumors, infectious diseases, drugs, etc.). The basic principle of such testing technology is established on specific binding properties between immune molecules, such as antibodies and antigens, haptens/antibodies, biotin and avidin, and so on.

The immunochromatography assay technology is applied by using blood as a sample for disease testing. At present, a variety of different diagnostic reagents have been developed and applied to different disease testing fields, for example, testing of tumor markers, early prognosis of cardiovascular diseases, screening testing of infectious diseases, etc. Blood, as a commonly used sample source, especially fingertip blood, has been widely adopted by various platforms due to its minimally invasive and rapid blood collection.

Moreover, in the field of medical diagnosis, it is a relatively common method to use a testing device or a testing cup to collect a liquid sample to be tested and determine whether the liquid sample contains an analyte. Such a testing device or testing cup generally requires that a sample is collected in a sample container. A relevant technician inserts a testing reagent strip and immerses part of the reagent strip in the sample. After a certain period of time, the reagent strip is taken out and the test result is read.

In the patent application No. CN201410150547.X in the prior art, a disposable storage container with one sealed end and one open end is disclosed to collect samples and store the same, and then it is inserted into a sample adding hole in a testing plate for sample addition to perform testing. In this patent application, the structure for collecting blood and the structure for testing samples are separately designed.

However, the existing testing devices have the following problems:
1. Most of the testing devices are of a separate structure and operated separately. The operation requirements are relatively high, and there are cases where the blood sample is contaminated or the blood sample contaminates an operator.
2. The structures of the testing devices are not small enough to be portable.

SUMMARY

The present invention also provides a blood collection structure, which is integrated into a testing device so that the testing device can be of an integrated structure, thereby not only reducing the volume of the testing device, but also realizing integrated testing and convenient operation.

Specifically, the present invention provides a blood collection structure, including a collection rod; a capillary channel is arranged inside the collection rod, the bottom end of the capillary channel is located at the tail end of the collection rod, and the top end of the capillary channel is located at the middle-upper part of the collection rod; and the collection rod is provided with a communicating hole connected to and communicated with the top end of the capillary channel.

In some preferred implementations, the outer surface of the collection rod is provided with a groove, the groove is located between the communicating hole and the top end of the collection rod, and one end of the groove is in communication with the communicating hole.

In some preferred implementations, the top end of the collection rod is provided with a barb, the bottom of the hook slot of the barb is provided with a through hole; the other end of the groove is connected with the barb and in communication with the through hole.

In some preferred implementations, the capillary channel, the communicating hole, the groove, and the hook slot and through hole of the barb on the collection rod form a liquid circulation channel.

In some preferred implementations, the tail end of the collection rod is tapered.

In some preferred implementations, an annular disc and an annular gasket sleeved on the collection rod are arranged in the middle of the collection rod.

In some preferred implementations, a plurality of ribs protruding out of the collection rod are arranged between the tail end of the collection rod and the annular disc.

In some embodiments, the rib has a right-triangle structure.

On the other hand, the present invention also provides a whole blood and fingertip blood testing device with an integrated structure, which enables integration of collection and testing of a blood sample, reduces product structure, reduces the operation difficulty of a testee, makes an operator contact the sample as little as possible, reduces the chance of infection, and improve the safety of the operator. In addition, by use of the blood collection structure and the whole blood and fingertip blood testing device, the sample can be made full use for testing, so that the demanded quantity of the sample is greatly reduced, which is more conducive to success of the testing.

Specifically, the whole blood and fingertip blood testing device provided by the present invention includes a blood collection structure, the blood collection structure includes a collection rod, a capillary channel is arranged inside the collection rod, the bottom end of the capillary channel is located at the tail end of the collection rod, and the top end of the capillary channel is located in the middle of the capillary channel; and the collection rod is provided with a communicating hole connected to and communicated with the top end of the capillary channel.

In some preferred implementations, the outer surface of the collection rod is provided with a groove, the groove is located between the communicating hole and the top end of the collection rod, and one end of the groove is in communication with the communicating hole.

In some preferred implementations, the top end of the collection rod is provided with a barb, the bottom of the hook slot of the barb is provided with a through hole; the other end of the groove is connected with the barb and in communication with the through hole; and the capillary channel, the communicating hole, the groove, and the hook slot and through hole of the barb on the collection rod form a liquid circulation channel.

In some preferred implementations, the tail end of the collection rod is tapered.

In some preferred implementations, the collection rod is provided with an annular disc and an annular gasket sleeved on the collection rod.

In some preferred implementations, the testing device also includes a testing chamber connected with and in fluid communication with the blood collection structure; and the inner wall of the testing chamber is provided with a first step, and the testing chamber is connected to the blood collection structure by clamping the first step with the barb. In a specific implementation, the open end of the barb clamps the first step to connect the testing chamber with the blood collection structure.

In some preferred implementations, the top end of the collection rod is inserted into the testing chamber from the bottom of the testing chamber, the tail end of the barb enters the testing chamber, then the open end of the barb is compressed, and the top end of the collection rod and the barb enter the testing chamber. After the open end of the barb reaches the first step, as the inner diameter of the testing chamber increases, the open end of the barb springs back to recover its original shape, and the barb is clamped at the first step. At this time, the bottom of the testing chamber forms sealing with the annular disc through the annular gasket.

In some preferred implementations, the inner wall of the testing chamber is also provided with a second step located above the first step; the whole blood and fingertip blood testing device also includes a cushion; and the cushion is located on the second step.

In some preferred implementations, the whole blood and fingertip blood testing device also includes a test element located in the testing chamber and a cover for sealing the testing chamber.

In some preferred implementations, the test element is located between the cushion and the cover.

In some preferred implementations, liquid entering the testing chamber through the collection rod flows into the cushion first, and then flows from the cushion onto the test element located in the testing chamber. The function of the cushion is to prevent washing liquid on an absorbing element from being too violent and abundantly and abruptly flowing into the testing chamber and onto the test element located in the testing chamber, thereby playing a role of buffering.

In some preferred implementations, the testing device also includes a bracket, and the bracket is provided with a depressed hole. The test element is a test strip, and the test strip is inserted into the depressed hole in the bracket for fixing. In some implementations, one end of the bracket is fixed to the cover.

In some preferred implementations, the testing device also includes a buffer chamber, a sealing sheet for sealing the buffer chamber, and a pipetting chamber; the bottom of the pipetting chamber is connected to the buffer chamber in a sealing manner; and a buffer solution is sealed in the buffer chamber.

In some preferred implementations, the pipetting chamber has a large cavity at the upper art and a small cavity at the lower part; and the bottom of the small cavity is connected to the buffer chamber in a sealing manner.

In some implementations, the sealing sheet is an aluminum foil.

In some preferred implementations, the outer wall of the bottom of the testing chamber is provided with a sealing gasket, the blood collection structure and the testing chamber enter into the pipetting chamber, and sealing is formed between the testing chamber and the pipetting chamber through the sealing gasket.

In some preferred implementations, first, the blood collection structure connected to the testing chamber is inserted into the pipetting chamber, and the tail end of the collection rod of the blood collection structure is located directly above the opening of the pipetting chamber; second, the blood collection structure continues to move along the direction that it is inserted into the pipetting chamber, the tail end of the collection rod contacts the sealing sheet, that is, the tail end of the collection rod reaches the top of the buffer chamber; third, the blood connection structure continues to move along the direction that it is inserted into the pipetting chamber, the tail end of the collection rod pierces the sealing sheet, the collection rod enters the buffer chamber, and part of the buffer solution is mixed with part of the sample in the capillary channel of the collection rod; fourth, the blood collection structure continues to move along the direction that it is inserted into the pipetting chamber, and the sealing gasket on the outer wall of the testing chamber forms sealing with the small cavity at the lower part of the pipetting chamber; and finally, the blood collection structure continues to move along the direction that it is inserted into the pipetting chamber, the space of the sealed cavity formed by the small cavity and the buffer chamber is compressed, the pressure in the cavity increases, the buffer solution rushes into the capillary channel to be mixed with the sample, and the mixed liquid flows into the testing chamber through the capillary channel, the communicating hole, the groove, and the hook slot and through hole of the barb on the collection rod.

In some preferred implementations, the testing chamber is transparent or is provided with a transparent window.

In some preferred implementations, one or more test elements can be provided. The plurality of test elements can test different analytes in the sample respectively.

In some preferred implementations, the testing chamber is in threaded connection with the pipetting chamber.

In some preferred implementations, the cushion is in contact with the test element(s).

In some preferred implementations, the cover spirally covers and seals the testing chamber.

On the other hand, the present invention also provides a method for collecting and testing a blood sample, involving a whole blood and fingertip blood testing device. The testing device includes a testing chamber and a blood collection structure, the inner wall of the testing chamber is provided with a first step, the blood collection structure includes a collection rod, the top end of the collection end is provided with a barb, and the testing chamber is connected to the blood collection structure by clamping the first step with the barb. A capillary channel is arranged inside the collection rod, the bottom end of the capillary channel is located at the tail end of the collection rod, and the top end of the capillary channel is located in the middle of the collection rod. The collection rod is provided with a communicating hole connected to and communicated with the top end of the capillary channel. The outer surface of the collection rod is provided with a groove, the groove is located between the communicating hole and the top end of the collection rod, and one end of the groove is in communicated with the communicating hole. The other end of the groove is connected to and communicated with the barb. The whole blood and fingertip blood testing device also includes a buffer chamber, a sealing sheet for sealing the buffer chamber, and a pipetting chamber; the bottom of the pipetting chamber is connected with the buffer chamber in a sealing manner. The buffer solution is sealed in the buffer chamber. The method includes: using the blood collection structure to collect a sample so that the capillary channel is filled with the blood sample; inserting the blood collection structure filled with the blood sample and the testing chamber connected to the blood collection structure into the pipetting chamber; enabling the blood collection structure to move in the pipetting chamber along the direction that it is inserted into the pipetting chamber, so that the blood collection structure reaches the sealing sheet; enabling the blood collection structure to pierce the sealing sheet on the buffer chamber and enter the buffer chamber, so that the sample in the capillary channel is mixed with the buffer solution; enabling the mixed liquid to flow onto the test element in the testing chamber along the capillary channel, the communicating hole, the groove, and the barb on the collection rod to perform testing; and reading the test result on the test element.

In some preferred implementations, the bottom of the hook slot of the barb is provided with a through hole; the other end of the groove is connected with the barb and in communication with the through hole; and the mixed liquid flows into the testing chamber through a liquid circulation channel formed by the capillary channel, the communicating hole, the groove, and the hook slot and through hole of the barb on the collection rod.

In some preferred implementations, the tail end of the collection rod is tapered; and the sealing sheet is pierced through the tapered tail end of the collection rod.

In some preferred implementations, the testing device also includes a cover covering the testing chamber, and after the cover covers the testing chamber, the test element is located in the testing chamber.

In some preferred implementations, the inner wall of the testing chamber is also provided with a second step located above the first step; a cushion is arranged in the testing chamber; the cushion is located on the second step; and after flowing into the testing chamber, the mixed liquid flows into the cushion first, and then flows from the cushion onto the test element located in the testing chamber.

In some preferred implementations, the outer wall of the bottom of the testing chamber is provided with a sealing gasket, the blood collection structure and the testing chamber enter into the pipetting chamber, and sealing is formed between the testing chamber and the pipetting chamber through the sealing gasket.

In some preferred implementations, the collection rod is provided with an annular disc and an annular gasket sleeved on the collection rod, and the bottom of the testing chamber forms sealing with the annular disc through the annular gasket.

Beneficial Effects

Through the integrated structure of the blood collection structure, the testing chamber and the buffer chamber, the whole blood and fingertip blood testing device according to the present invention achieves functions of collecting, slowly releasing and testing the blood sample. First, the operation of the testing device is easy, which reduces the difficulty of use by the operator. Second, the number of times and time that the operator contacts the sample are effectively reduced, the infectious possibility of the operator is reduced, and the safety of the operator is ensured, so that the testing device is particularly suitable for HIV testing, novel coronavirus testing, etc. Third, the integrated testing device is provided with the buffer solution therein, so that the collected amount of the sample is required to be small, and is optimized from the milliliter level to the microliter level. Finally, due to the integrated structure, collection, slow release and testing are realized in one step, thereby improving the success rate of the testing.

REFERENCE SIGNS

Whole blood and fingertip blood testing device 100, blood collection structure 10, collection rod 11, capillary channel 111, communicating hole 112, groove 113, barb 114, hook slot 115, through hole 116, open end 119 of barb, top end 117 of collection rod, tail end 118 of collection rod, annular disc 120, annular gasket 121, rib 122, testing chamber 20, first step 21, second step 22, cushion 23, transfer chamber 30, large cavity 31, small cavity 32, buffer chamber 40, gasket 41, test element 50, sample reception area 501, test area 502, buffer solution 60, sealing sheet 70, sealing gasket 80, cover 90, bracket 51, depressed hole 52.

DETAILED DESCRIPTION OF EMBODIMENTS

The structure involved in the present invention or these technical terms used will be further illustrated below.

Testing

Testing represents to assay or test the presence of a substance or material, such as, but not limited to, chemical substances, organic compounds, inorganic compounds, metabolites, drugs or drug metabolites, organic tissues or metabolites of organic tissues, nucleic acids, proteins or polymers. In addition, testing represents the quantity of the test substance or material. Further, assay also represents immunoassay, chemical testing, enzyme testing, etc.

Sample

The sample referred to in the present invention refers to those substances that can be used to test, or diagnose the presence of the analyte of interest. The sample may be, for example, a liquid sample, which can include blood, plasma and serum, and may also include a liquid solution formed by a solid sample and a semi-solid sample after pretreatment. The collected sample can be used for methods such as immunoassay, chemical testing and enzyme testing to test the presence of the analyte. In a preferred embodiment, the sample in the present invention is a blood sample.

Analyte

With the device and method according to the present invention, any analyte can be analyzed. The analyte can be tested in any liquid or liquefied specimen, such as blood, plasma or serum.

The analyte may also be some hapten substances, which include narcotics (such as drugs of abuse). "Drugs of abuse" (DOA) refers to the use of drugs for non-medical purposes (usually playing a role of paralyzing nerves). The device may also be used to test drugs which are for medical purposes but easy to overdose, such as tricyclic antidepressants (imipramine or analogues) and acetaminophen. These drugs are decomposed into different small molecular substances after being absorbed by the human body. These small molecular substances are present in blood, urine, saliva, sweat and other body fluids, or some of the body fluids contain the above-mentioned small molecular substances. The device may also be used for testing of antibodies to the new coronavirus and testing of neutralizing antibodies after vaccination of new coronavirus vaccines.

Test Element 50

The test element 50 can be a lateral flow test strip, which can test a variety of analytes. Of course, other suitable test elements may also be used in the present invention. Various test elements can be combined together for use in the present invention. One form of the test element is test paper. The test paper used to analyze the analyte in a sample (such as narcotics or metabolites indicating physical conditions) can be in various forms, such as immunoassay or chemical analysis. The test paper can adopt the analysis mode of non-competitive law or competitive law. The test paper includes an absorbent material with a sample reception area, a reagent area and a test area. The sample is added to the sample reception area, and flows to the reagent area by capillary action. In the reagent area, the sample is bound to the reagent if the analyte is present. Then, the sample continues to flow to the test area. Other reagents, such as molecules that are specifically bound to the analyte, are immobilized in the test area. These reagents react with the analyte (if present) in the sample and bind the analyte into this area, or bind the analyte to some reagent in the reagent area. The marker used to display a test signal is present in the reagent area or a separated mark area.

The typical analysis mode of the non-competitive law is: if the sample contains the analyte, a signal will be generated, and if it does not contain the analyte, no signal will be generated. In the competitive law, if the analyte is not present in the sample, a signal will be generated, and if the analyte is present, no signal will be generated.

The test element 50 can be test paper, and can use an absorbent or nonabsorbent material. The test paper may include a variety of materials for delivery of liquid samples. One of the materials of the test paper can be covered on another material, such as filter paper covered on a nitrocellulose membrane. One area of the test paper can use one or more materials, and the another area can use one or more other different materials. The test paper can be adhered to some support or hard surface to improve the strength of holding the test paper. The analyte is tested by a signal generation system, for example, using one or more enzymes that specifically react with this analyte, and using the method of fixing the specifically bound substance on the test paper as above mentioned, and the composition of one or more signal generation systems is fixed in the analyte test area of the test paper. The substance that generates a signal can be in the sample reception area 501, or the reagent area, or the test area, or the entire test paper, and the substance can be filled in one or more materials of the test paper. The solution containing a signal substance is added to the surface of the test paper or one or more materials of the test paper are immersed in the solution containing the signal substance. The test paper to which the solution containing the signal substance is added is dried.

The various areas of the test paper can be arranged in the way below: the sample reception area, the reagent area, the test area, a control area, an area in which whether the sample is adulterated is determined, and a liquid sample absorption area. The control area is located behind the test area. All areas can be arranged on a test strip using only one material. It is also possible to use different materials for different areas. Each area can be in direct contact with the liquid sample, or different areas are arranged according to the flowing direction of the liquid sample, and the tail end of each area is connected to and overlapped with the front end of another area. The material used may be a material with good water absorption, such as filter paper, glass fiber or a nitrocellulose membrane. The test paper can also be in other forms.

Testing Chamber 20

The testing chamber 20 is generally a cavity for accommodating the test element 50 and enables the liquid sample to enter into the cavity 20 to contact the test element 50 for testing. It is in various shapes, and can be designed according to the shape and number of the test elements 50 required to be accommodated. In the present invention, the test element is a test strip 50. Therefore, in one embodiment, the testing chamber 20 has a cylindrical structure, and the test strip 50 is located in the cylinder. In some other embodiments, the testing chamber 20 is provided with a cover 90 that seals an upper cavity opening, and the test strip 50 is fixed on the cover 90 so as to be located in the testing chamber 20 in a relatively fixed manner. In some other preferred implementations, the cylinder 20 has a window, and the position of the window corresponds to the test area of the test strip, which facilitates viewing the test result of the test strip. Or, in some other embodiments, the cylinder itself is transparent, which facilitates viewing the test result of the test strip. In other embodiments, the test strip is fixed in the hollow cylinder by a bracket 51. Specifically, the bracket is provided with a depressed hole 92, and the test strip is inserted into the depressed hole.

In the following detailed description, the reference text attached to the legends is a part herein, and it is described in a manner of exemplifying specific solutions that the present invention may implement. We do not exclude that the present invention also can implement other specific solutions and the structure in the present invention can be changed without departing from the usage scope of the present invention.

As shown in FIGS. 1-8, in the present invention, the blood collection structure includes a collection rod 11, the two ends of the collection rod are a top end 117 of the collection rod and a tail end 118 of the collection rod, and a capillary channel 111 is arranged inside the collection rod. The capillary channel does not penetrate through the entire collection rod, the bottom of the capillary channel is located at the tail end 118 of the collection rod, and the top of the capillary channel is located at the middle-upper part of the collection rod 11. The capillary channel 111 is used to collect a blood sample, and more preferably, it is usually used to collect a whole blood sample. The collection rod 11 is also provided with a communicating hole 112 connected to and communicated with the top of the capillary channel 111. The communicating hole 112 transversely penetrates through the collection rod 11, so that the liquid in the capillary channel 111 can flow out of the collection rod 11 through the communicating hole 112. In some embodiments, the diameter of the capillary channel is between 0.1 mm and 2 mm. In a specific embodiment, the diameter of the capillary channel is between 0.1 mm and 1.7 mm. In addition, the outer surface of the collection rod 11 is provided with a groove 113. The groove 113 is longitudinally arranged on the outer surface of the collection rod 11, and is located between the communicating hole 112 and the top end 117 of the collection rod, and one end of the groove 113 is communicated with the communicating hole 112, so as to realize communication with the communicating hole 112.

Figure 3:
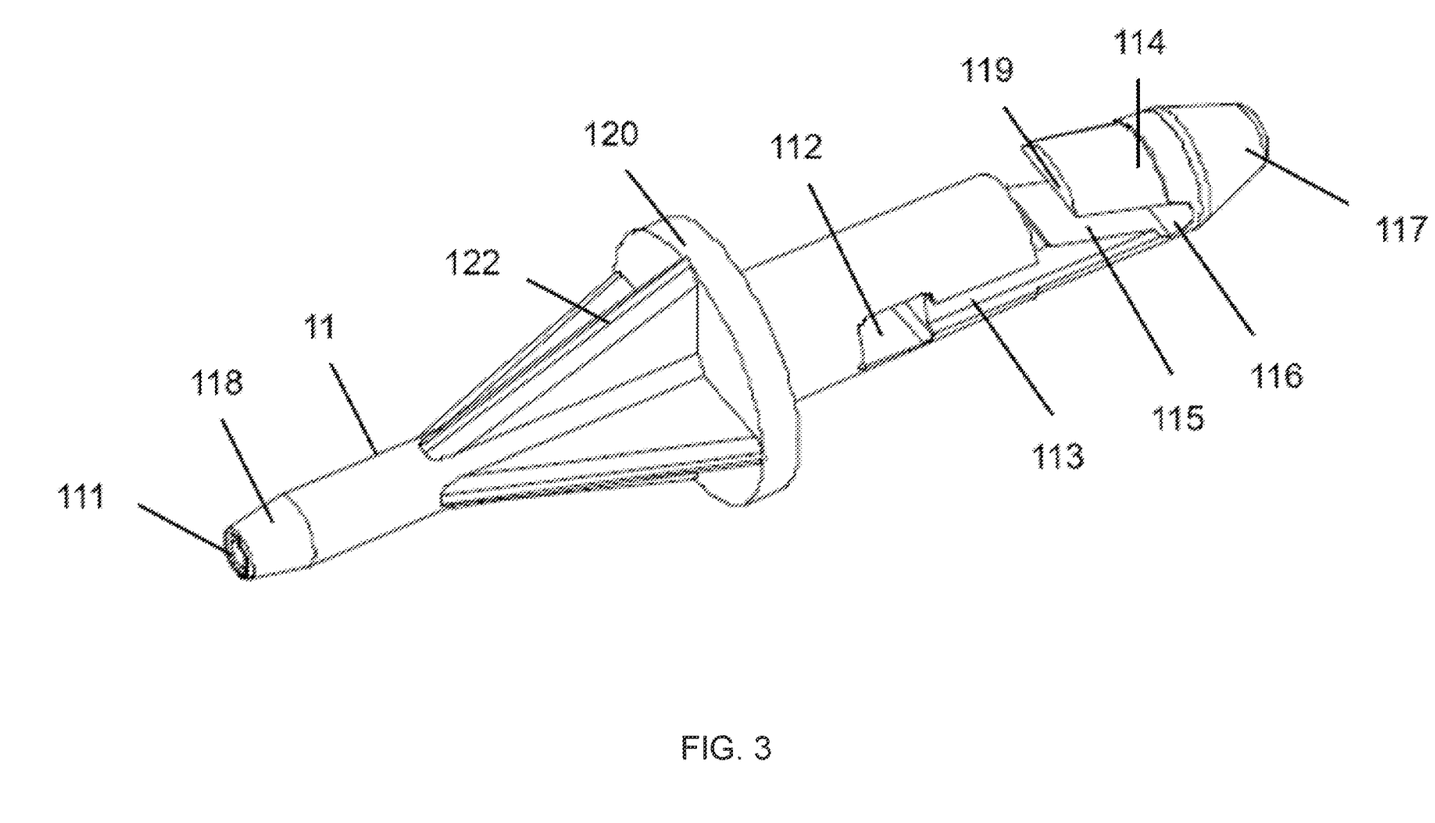
FIG. 3 is a schematic diagram of a blood collection structure according to the present invention.
Figure 4:
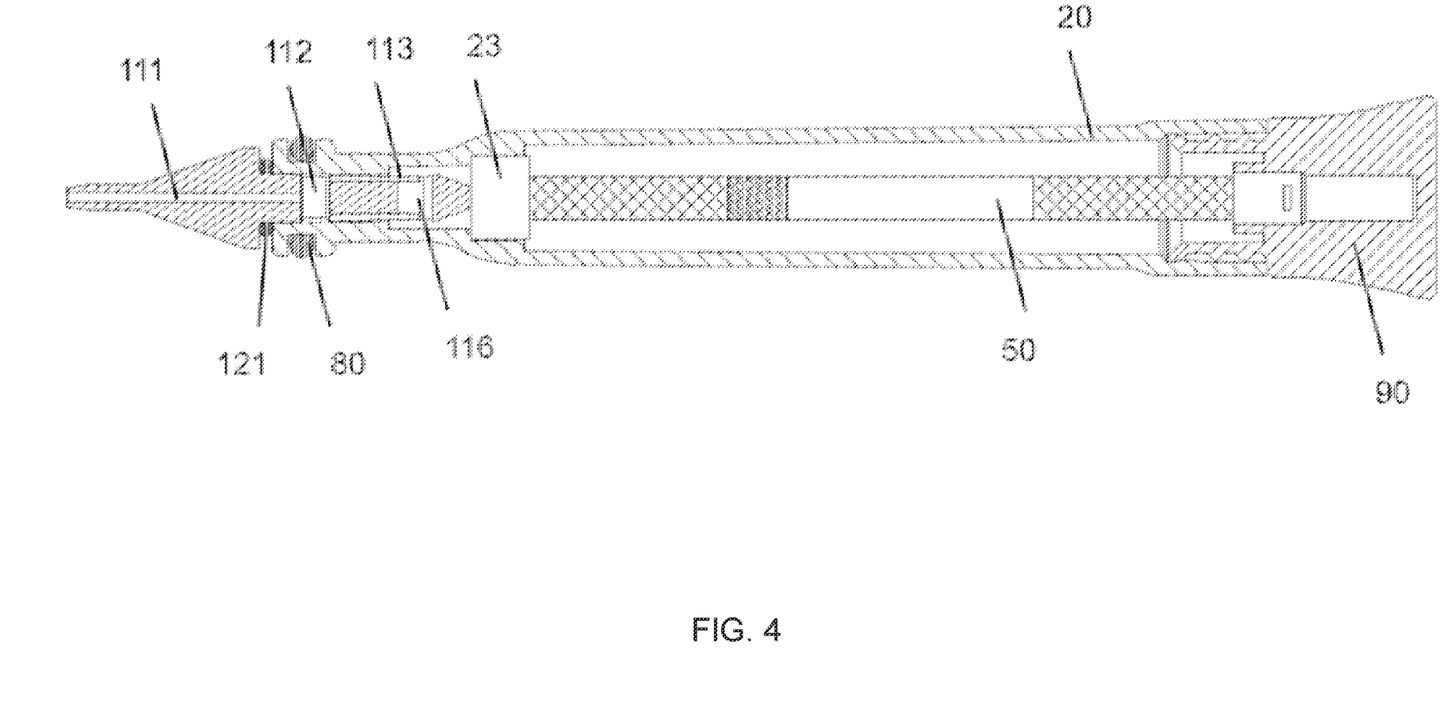
FIG. 4 is a schematic cross-sectional view of the blood collection structure and a testing chamber in the present invention.
Figure 5:
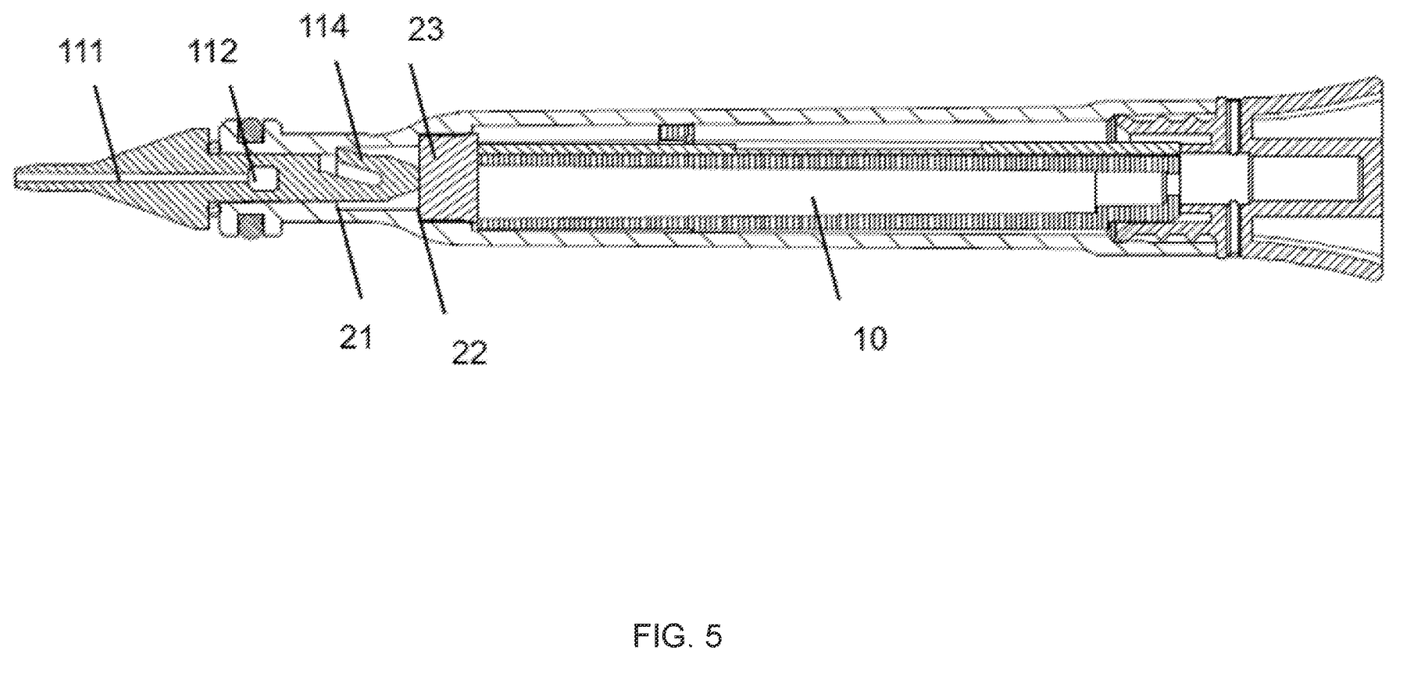
FIG. 5 is a schematic cross-sectional view of the blood collection structure and the testing chamber in the present invention.
Figure 6:
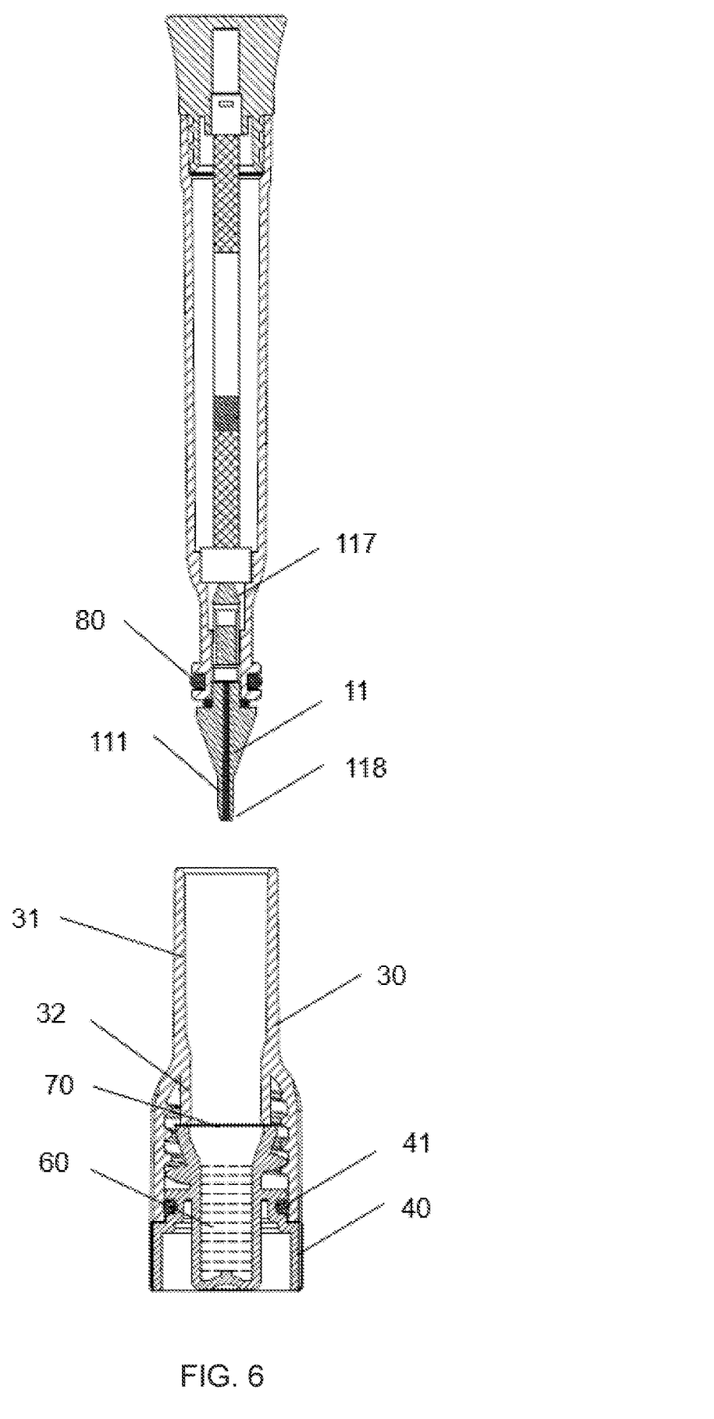
FIG. 6 is a cross-sectional view of the whole blood and fingertip blood testing device according to the present invention before starting of use.

The top end 117 of the collection rod is provided with a barb 114. As shown in FIG. 3, the barb 114 is hollowed out in the middle to form a hook slot 115. When a pressure is applied, the open end 119 of the barb 114 will move towards the hollow hook slot 115, so that the outer peripheral surface of the entire barb 114 is reduced, which facilitates entrance into a cavity of a certain volume; and when the pressure disappears, the open end 119 of the barb 114 will return to its original position. The hook bottom of the barb 114 has a through hole 116 larger than the hook slot 115; and the other end of the groove 113 is connected to the barb 114 and communicated with the through hole 116. Therefore, the hook slot 115 can not only cause the open end 119 of the barb to deform elastically inward, but also can cause fluid communication of the groove located on the outer surface of the collection rod with the communicating hole at the tail end of the hook slot, so that the capillary channel 111, the communicating hole 112, the groove 113, and the hook slot 115 and through hole 116 of the barb on the collection rod 11 form a liquid circulation channel. More specifically, the tail end of the barb 116 is set to be tapered, and in this way, the top end 117 of the collection rod can easily enter into the cavity.

In an embodiment, the tail end 118 of the collection rod is tapered. In this way, the tapered tail end of the collection rod can pierce thinner sheet-like objects, such as metal sheets (such as an aluminum foil and a tin foil), or paper sheets, plastic sheets, or the like. Moreover, in an embodiment, the top end 117 of the collecting rod is also set to be tapered, which facilitates entrance of the top end 117 of the collection rod into the cavity.

In addition, the collection rod 11 is provided with an annular disc 120 and an annular gasket 121 sleeved on the collection rod, and the annular gasket is located between the annular disc 120 and the top end 117 of the collection rod. A plurality of ribs 122 protruding out of the collection rod are arranged between the tail end 118 of the collection rod and the annular disc 120. In some embodiments, the rib 122 has a right-triangle structure. In this way, after the part of the collection rod below the annular disc 120 enters the hollow cavity, it is able to occupy the space of the hollow cavity to a greater extent, so that the space in the hollow cavity is squeezed to be decreased.

As shown in FIGS. 1-8, the whole blood and fingertip blood testing device 100 according to the present invention first includes the aforementioned blood collection structure 10, and also includes a testing chamber 20, and the testing chamber 20 and the blood collection structure 10 are fixedly connected. Specifically, the testing chamber 20 has a cylindrical structure, the inner diameter of the cylinder changes stepwise, there are three segments of different inner diameters in total, and from the bottom to the top of the testing chamber 20, the inner diameter of the cavity gradually increases stepwise. Therefore, the inner wall of the testing chamber 20 has a first step 21 and a second step 22. The top end 117 of the collection rod is inserted from the bottom of the testing chamber 20. The outer circumference at the barb 114 on the collection rod is larger than the inner circumference of the bottom of the testing chamber 20. The barb 114 is compressed and the open end sinks into the cavity in the middle, so that the outer circumference of the barb 114 is adapted to the inner circumference of the bottom of the testing chamber. The top end 117 of the collection rod enters the testing chamber 20 until the entire barb 114 is located at the first step 21. As the inner diameter at the first step 21 of the testing chamber 20 increases, the barb 114 is not compressed, and the open end 119 returns to the original position. In this way, the diameter of the entire barb 114 is larger than the inner diameter of the testing chamber 20 below the first step 21. Therefore, the barb 114 is clamped at the first step 21 to fixedly connect the collection rod 11 to the testing chamber 20, so that the blood collection structure 10 and the testing chamber 20 are also fixedly connected. At this time, between the bottom of the testing chamber 20 forms sealing with the annular disc 120 through the annular gasket 121, so that the blood collection structure 10 forms sealing with the testing chamber 20.

Figure 1:
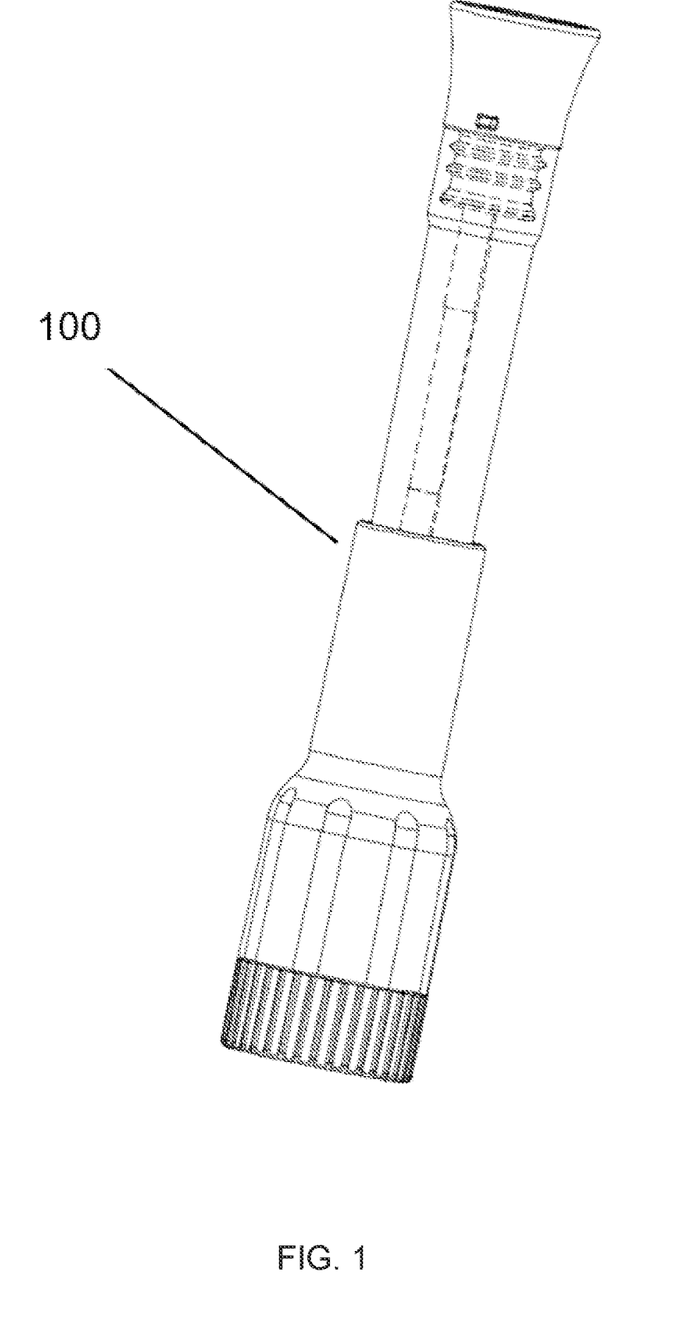
FIG. 1 is a schematic structural diagram of a whole blood and fingertip blood testing device according to the present invention.
Figure 2:
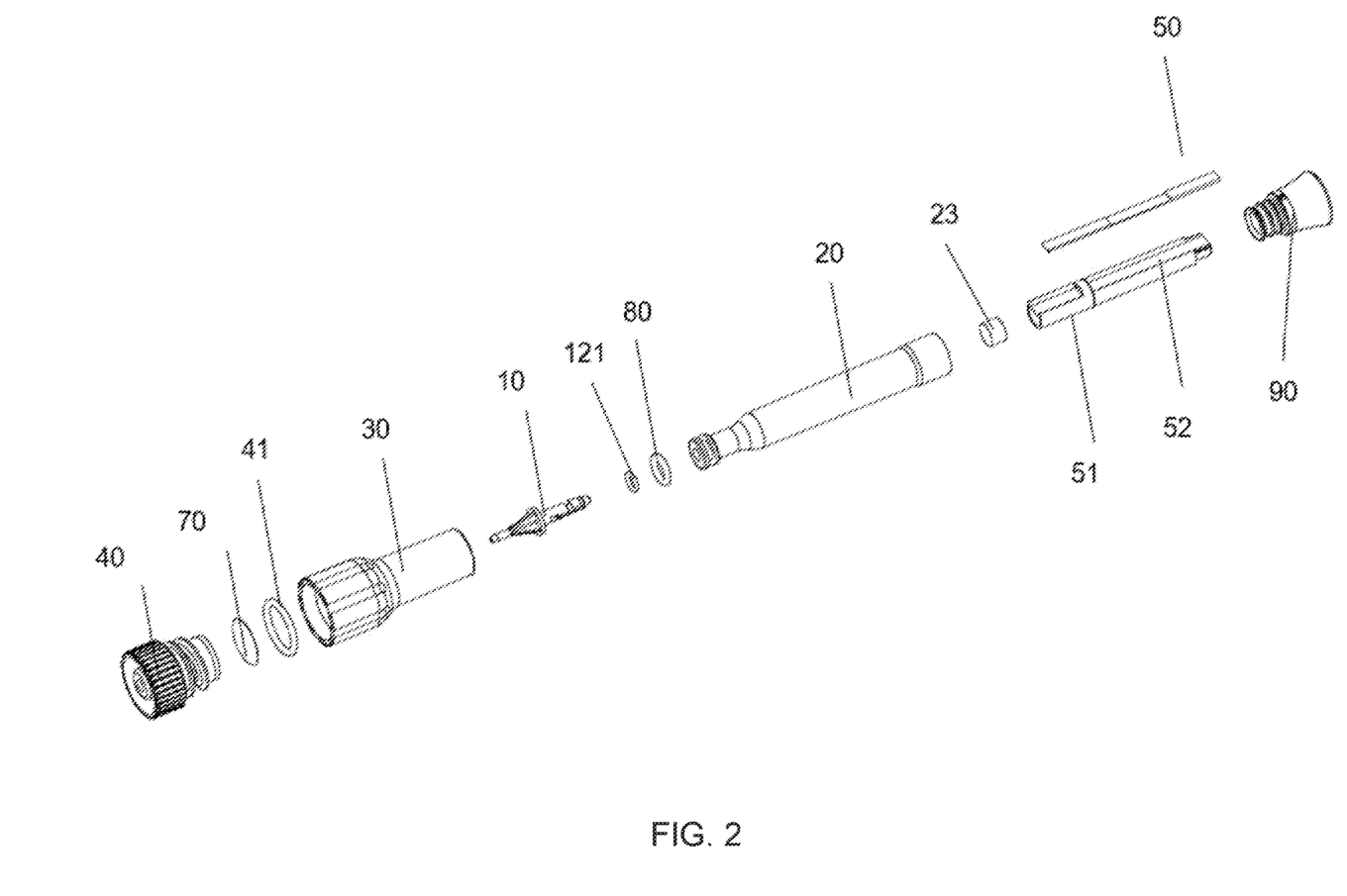
FIG. 2 is a schematic exploded view of the whole blood and fingertip blood testing device according to the present invention.

A cover 90 is arranged on the top of the testing chamber 20, and the cover 90 seals the testing chamber 20. In one embodiment, the cover 91 spirally covers the testing chamber 20. At the same time, in the present invention, the cover 90 is also used to fix the test element 50. In one embodiment, the test element 50 is a test strip. Specifically, a plurality of test strips can be provided for testing of different analytes. The cover 90 is provided with a clamping slot for clamping the tail end of the test strip 50 so that the test strip 50 is fixed on the cover 90. In some other embodiments, as shown in FIG. 2, a bracket 91 is buckled on the top inside the cover, and the bracket 91 is used to fix the test strip. More specifically, a strip-shaped depressed hole 91 is formed in the bracket, and the test strip is placed and fixed in the depressed hole. Of course, a plurality of strip-shaped depressed holes can be formed in the bracket to fix the plurality of test strips. After the cover 90 covers the testing chamber 20, the test strip 50 is fixedly located in the testing chamber 20.

In order to enable the liquid to slowly flow to the test element 50, namely, the sample reception area 501 of the test strip, and to also prevent excessive liquid from entering the testing chamber 20, the test area 502 of the test element 50 (test strip) is also submerged to ensure the validity of the testing, and a cushion 23 is placed on the second step 22 located above the first step 21. In some preferred embodiments, the end of the sample reception area of the test element 50 is in zero-clearance contact with the cushion 23, which can ensure that the test element 50 absorbs enough liquid to ensure the success rate of the testing.

The liquid in the capillary channel flows into the testing chamber 20 after circulation through the communicating hole and the groove as well as the hook slot and the through hole, then reaches the cushion 23 for buffering, and finally flows onto the test element 50 for testing.

In the present invention, some samples, before testing, need to be mixed with a buffer solution 60 for slow release. Therefore, this sample collection and testing device further includes a buffer chamber 40 in which the buffer solution 60 is stored, and includes a sealing sheet 70 for sealing the buffer solution in the buffer chamber. The device also includes a pipetting chamber 30 that is connected to the buffer chamber in a sealing manner. The pipetting chamber 30 is used to receive the blood collection structure 10 and transfer the buffer solution 60 to the blood collection structure 10 and the testing chamber 20. In a specific embodiment, the buffer chamber 40 and the pipetting chamber 30 are in threaded connection to form sealing therebetween. Specifically, a gasket 41 is arranged on the top of the outer wall of the buffer chamber. After the pipetting chamber 30 is spirally connected to the buffer chamber 40, the pipetting chamber and the buffer chamber are sealed by the gasket 41. In a specific embodiment, a clamping strip (not shown in the figure) is arranged in the pipetting chamber 30, and is used for cooperation with the ribs of the blood collection structure, so that the blood collection structure is relatively fixed in the pipetting chamber to avoid significant rotation of the blood collection structure 10 in the pipetting chamber 30 in the inserted process, so as to ensure a smoother operation.

In some embodiments, the outer wall of the bottom of the testing chamber 20 is provided with a sealing gasket 80, the blood collection structure 10 and the testing chamber 20 enter into the pipetting chamber 30, and the testing chamber 20 forms sealing with the inner wall of the pipetting chamber 30 through the sealing gasket 80. In the present invention, considering that the amount of a blood sample is small (only the part in the capillary channel), and the amount of a buffer solution matching the same is also small, in one embodiment, the cavity provided with the pipetting chamber 30 has a structure with a large upper part and a small lower part, that is, it includes a large cavity 31 at the upper part and a small cavity 32 at the lower part. After the sealing gasket 80 on the outer wall of the testing chamber contacts the small cavity 32 of the pipetting chamber, the small cavity 32 is sealed. In this way, the volume of the sealed cavity formed by the small cavity and the buffer chamber is relatively small. After the collection rod enters in, the volume of the sealed cavity is occupied by the collection rod and the ribs thereon, so that the space is significantly squeezed, and the blood sample and the buffer solution will be squeezed more to flow into the testing chamber through the capillary channel, the groove, the hook slot and the through hole to ensure that there are enough samples for the test element in the testing chamber to perform testing.

When in use, the blood collection structure 10 connected to the testing chamber 20 is inserted into the pipetting chamber 30. First, the tail end 118 of the collection rod of the blood collection structure is located directly above the opening of the pipetting chamber 30. Second, the blood collection structure 10 continues to move along the direction that it is inserted into the pipetting chamber 30, the tail end 118 of the collection rod contacts the sealing sheet 70, that is, the tail end 118 of the collection rod reaches the top of the buffer chamber 30. Third, the blood connection structure 10 continues to move along the direction that it is inserted into the pipetting chamber 30, the tail end 118 of the collection rod pierces the sealing sheet 70, the collection rod 11 enters the buffer chamber 30, and when the buffer solution in the collection rod contacts the tail end of the collection rod, that is, when the buffer solution contacts the bottom end of the capillary channel, part of the sample at the bottom end of the capillary channel of the collection rod is mixed with the buffer solution. Fourth, the blood collection structure 10 continues to move along the direction that it is inserted into the pipetting chamber 30, and the sealing gasket 80 on the outer wall of the testing chamber 20 forms sealing with the small cavity 32 at the lower part of the pipetting chamber 30. Finally, the blood collection structure 10 continues to move along the direction that it is inserted into the pipetting chamber 30, the space of the sealed cavity formed by the small cavity 32 and the buffer chamber 40 is gradually compressed due to gradual entrance of the collection rod below the annular disc, at the same time, the pressure in the cavity gradually increases, the buffer solution rushes into the capillary channel to be mixed with the sample, and the mixed liquid flows into the testing chamber through the capillary channel, the communicating hole, the groove, and the hook slot and through hole of the barb on the collection rod.

The method for collecting and detecting a sample using the sample collection and testing device according to the present invention will be described in detail below.

First, the whole blood and fingertip blood testing device 100 seals the buffer solution 60 in the buffer chamber 40 in the production process, and the sealing sheet 70 is fixed at the opening of the buffer chamber 40; the pipetting chamber 30 is spirally connected to the buffer chamber 40, and the bottom of the pipetting chamber and the top of the buffer chamber are sealed by the gasket 41; the blood collection structure 10 is connected to the first step 21 of the testing chamber 20 through the barb 114 at the top end 117 of the collection rod so that the blood collection structure 10 and the testing chamber 20 are relatively fixed, wherein the blood collection structure and the bottom of the testing chamber 20 are sealed through the annular disc and the annular gasket, and the collection rod 11 below the annular disc is exposed outside the testing chamber 20; and in the initial state, in order to keep clean and sanitary, the part of the collection rod exposed outside the testing chamber 20 is individually packaged in a plastic bag in advance.

Second, the plastic bag is torn and removed, the sample is collected through the capillary channel of the collection rod (for example, the capillary channel at the tail end of the collection rod is aligned to a pierced and bleeding point on a fingertip of a testee, or the capillary channel at the tail end of the collection rod is put into a container in which a liquid sample is collected to absorb the sample), so that the capillary channel 111 is filled with the liquid sample, usually a blood sample.

Figure 7:
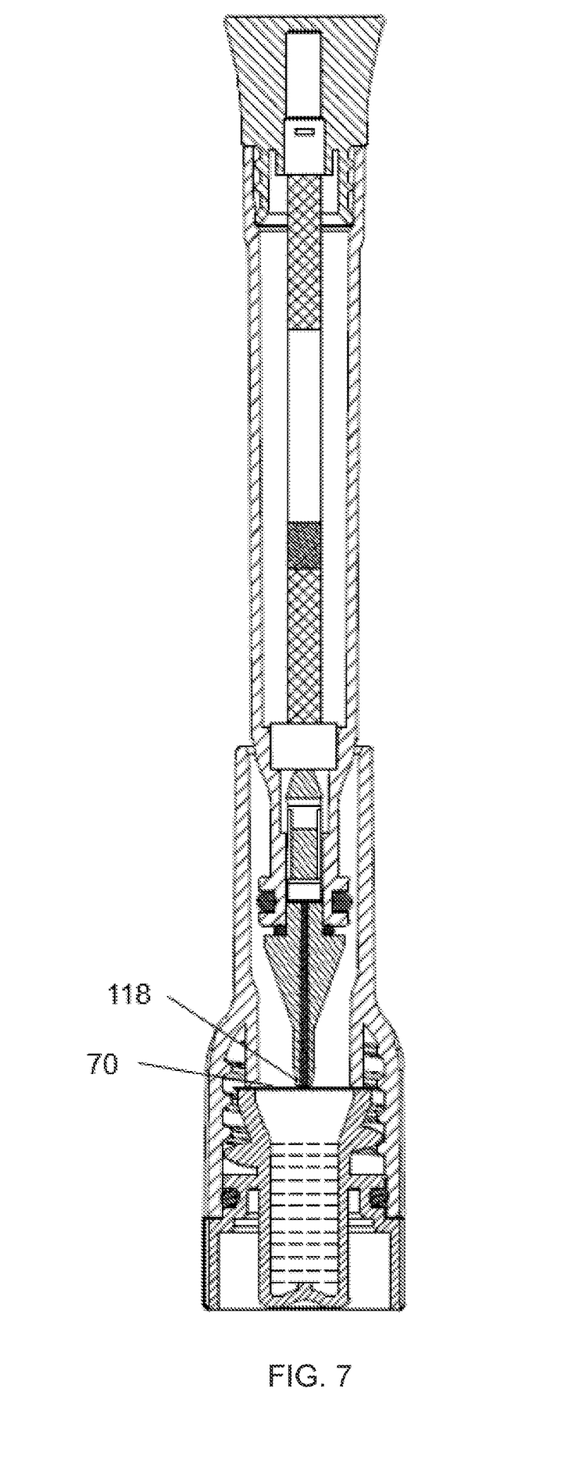
FIG. 7 is a cross-sectional view showing that the blood collection structure of the whole blood and fingertip blood testing device according to the present invention reaches a buffer chamber.

Third, the blood collection structure 10 filled with a liquid sample, together with the testing chamber 20 connected thereto is displaced to a position directly above the opening of the pipetting chamber 30, as shown in FIG. 7; and then the blood collection structure 10 and the testing chamber 20 connected thereto are inserted into the pipetting chamber 30 through the tail end 118 of the collection rod.

Fourth, the blood collection structure 10 moves in the pipetting chamber 30 along the direction that it is inserted into the pipetting chamber 30 until the tapered tail end 117 of the collection rod of the blood collection structure reaches the sealing sheet 70, that is, the tail end 117 of the collection rod reaches the top of the buffer chamber 40, as shown in FIG. 7.

Fifth, the blood collection structure 10 continues to move in the pipetting chamber 30 in the direction that it is inserted into the pipetting chamber 30, the tail end of the collection rod pierces the sealing sheet, the collection rod enters the buffer chamber, and when the buffer solution contacts the bottom end of the capillary channel, part of the sample in the capillary channel of the collection rod is mixed with the buffer solution.

Sixth, the blood collection structure 10 and the testing chamber 20 continue to move in the same direction, and the sealing gasket on the outer wall of the testing chamber forms sealing with the small cavity at the lower part of the pipetting chamber.

Figure 8:
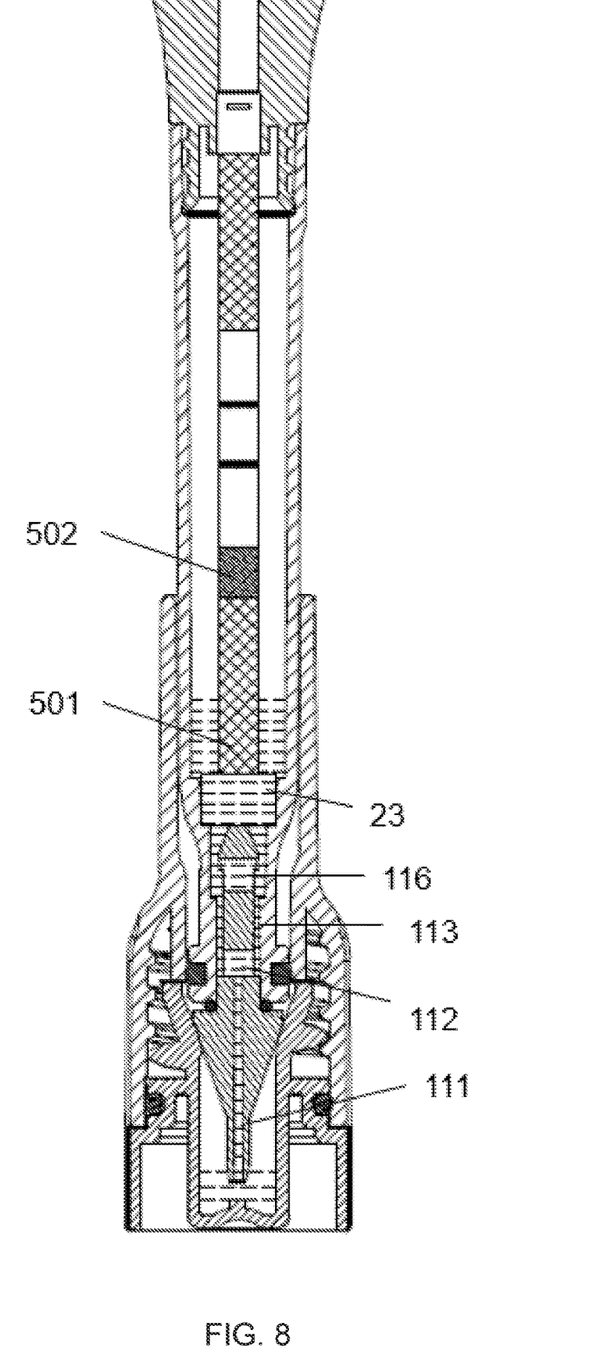
FIG. 8 is a cross-sectional view showing that the blood collection structure of the whole blood and fingertip blood testing device according to the present invention reaches the sample in the buffer chamber for buffering and testing.

Seventh, the blood collection structure continues to move in the direction that it is inserted into the pipetting chamber, the space of the sealed cavity formed by the small cavity and the buffer chamber is compressed, the pressure in the cavity increases, the buffer solution rushes into the capillary channel to be mixed with the sample, and the mixed liquid flows into the testing chamber through the capillary channel, the communicating hole, the groove, and the hook slot and through hole of the barb on the collection rod, as shown in FIG. 8.

Eighth, the test result on the test element 50 is read to complete the testing.

What is claimed is:

1. A whole blood and fingertip blood testing device, comprising a blood collection structure and a testing chamber, wherein the blood collection structure comprises a collection rod, a capillary channel is arranged inside the collection rod, a bottom end of the capillary channel is located at a tail end of the collection rod, and a top end of the capillary channel is located in a middle-upper part of the collection rod; and the collection rod is provided with a communicating hole connected to and communicated with the top end of the capillary channel;

an outer surface of the collection rod is provided with a groove, the groove is located between the communicating hole and a top end of the collection rod, and one end of the groove is in communication with the communicating hole;

the top end of the collection rod is provided with a barb, a bottom of a hook slot of the barb is provided with a through hole; and the other end of the groove is connected with the barb and in communication with the through hole; and the capillary channel, the communicating hole, the groove, the hook slot, and the through hole of the barb on the collection rod form a liquid circulation channel, the liquid circulation channel being configured to transport a blood sample to the testing chamber for detection, wherein the tail end of the collection rod is tapered, and the collection rod is provided with an annular disc and an annular gasket sleeved on the collection rod;

the testing chamber is connected with and in fluid communication with the blood collection structure, an inner wall of the testing chamber is provided with a first step, and the testing chamber is connected to the blood collection structure by clamping the first step with the barb;

the top end of the collection rod is configured to be inserted into the testing chamber from a bottom of the testing chamber, a tail end of the barb is configured to enter the testing chamber;

an open end of the barb is configured to be compressed, and the top end of the collection rod and the barb are configured to enter the testing chamber; and the open end of the barb is configured to reach the first step, an inner diameter of the testing chamber is configured to increase, the open end of the barb is configured to spring back to recover its original shape, the barb is configured to be clamped at the first step, and the bottom of the testing chamber is configured to seal with the annular disc through the annular gasket.

2. The whole blood and fingertip blood testing device according to claim 1, wherein the inner wall of the testing chamber is also provided with a second step located above the first step; the whole blood and fingertip blood testing device further comprises a cushion; the cushion is located on the second step; and the cushion is configured to receive the blood sample entering the testing chamber through the collection rod and transfer the blood sample onto a test element located in the testing chamber.

3. The whole blood and fingertip blood testing device according to claim 2, further comprising a cover for sealing the testing chamber, wherein the test element is located between the cushion and the cover.

4. The whole blood and fingertip blood testing device according to claim 1, further comprising a buffer chamber, a sealing sheet for sealing the buffer chamber, and a pipetting chamber, wherein a bottom of the pipetting chamber is connected to the buffer chamber in a sealing manner; and a buffer solution is sealed in the buffer chamber.

5. The whole blood and fingertip blood testing device according to claim 4, wherein an outer wall of the bottom of the testing chamber is provided with a sealing gasket, the blood collection structure and the testing chamber enter into the pipetting chamber, and sealing is formed between the testing chamber and the pipetting chamber through the sealing gasket.

6. The whole blood and fingertip blood testing device according to claim 5, wherein first, the blood collection structure connected to the testing chamber is configured to be inserted into the pipetting chamber, and the tail end of the collection rod of the blood collection structure is configured to be located directly above an opening of the pipetting chamber;

second, the blood collection structure is configured to continue to move along a direction that it is inserted into the pipetting chamber, the tail end of the collection rod is configured to contact the sealing sheet, the tail end of the collection rod is configured to reach a top of the buffer chamber;

third, the blood connection structure is configured to continue to move along the direction that it is inserted into the pipetting chamber, the tail end of the collection rod is configured to pierce the sealing sheet, the collection rod is configured to enter the buffer chamber, and the buffer solution is configured to be mixed with part of the blood sample in the capillary channel of the collection rod;

fourth, the blood collection structure is configured to continue to move along the direction that it is inserted into the pipetting chamber, and the sealing gasket on the outer wall of the testing chamber is configured to form sealing with a small cavity at a lower part of the pipetting chamber; and finally, the blood collection structure is configured to continue to move along the direction that it is inserted into the pipetting chamber, a space of a sealed cavity formed by the small cavity and the buffer chamber is configured to be compressed, a pressure in the small cavity is configured to increase, the buffer solution is configured to rush into the capillary channel to be mixed with the blood sample to form a mixed liquid, and the mixed liquid is configured to flow into the testing chamber through the capillary channel, the communicating hole, the groove, and the hook slot and through hole of the barb on the collection rod.

7. The whole blood and fingertip blood testing device according to claim 5, wherein the pipetting chamber includes a large cavity at an upper part and a small cavity at a lower part, the small cavity is configured to be sealed when the sealing gasket on the outer wall of the bottom of the testing chamber contacts the small cavity of the pipetting chamber.

8. The whole blood and fingertip blood testing device according to claim 1, wherein the whole blood and fingertip blood testing device further includes a test strip and a bracket, the test strip is fixed in the testing chamber by the bracket, wherein the bracket is provided with a depressed hole and the test strip is inserted into the depressed hole.

9. A method for collecting and testing a blood sample, involving a whole blood and fingertip blood testing device, wherein the testing device comprises a testing chamber and a blood collection structure, an inner wall of the testing chamber is provided with a first step, the blood collection structure comprises a collection rod, a top end of a collection rod is provided with a barb, and the testing chamber is connected to the blood collection structure by clamping the first step with the barb; a capillary channel is arranged inside the collection rod, a bottom end of the capillary channel is located at a tail end of the collection rod, and a top end of the capillary channel is located in a middle-upper part of the collection rod; the collection rod is provided with a communicating hole connected to and communicated with the top end of the capillary channel; an outer surface of the collection rod is provided with a groove, the groove is located between the communicating hole and the top end of the collection rod, and one end of the groove is in communicated with the communicating hole; the other end of the groove is connected to and communicated with the barb; the whole blood and fingertip blood testing device further comprises a buffer chamber, a sealing sheet for sealing the buffer chamber, and a pipetting chamber; a bottom of the pipetting chamber is connected with the buffer chamber in a sealing manner; a buffer solution is sealed in the buffer chamber; and wherein the method comprises:

using the blood collection structure to collect the blood sample so that the capillary channel is filled with the blood sample;

inserting the blood collection structure filled with the blood sample and the testing chamber connected to the blood collection structure into the pipetting chamber;

enabling the blood collection structure to move in the pipetting chamber along a direction that it is inserted into the pipetting chamber, so that the blood collection structure reaches the sealing sheet;

enabling the blood collection structure to pierce the sealing sheet on the buffer chamber and enter the buffer chamber, so that the sample in the capillary channel is mixed with the buffer solution to form a mixed liquid;

enabling the mixed liquid to flow onto a test element in the testing chamber along the capillary channel, the communicating hole, the groove, and the barb on the collection rod to perform testing; and reading a test result on the test element.

10. The method according to claim 9, wherein a bottom of a hook slot of the barb is provided with a through hole; the other end of the groove is connected with the barb and in communication with the through hole; and the mixed liquid flows into the testing chamber through a liquid circulation channel formed by the capillary channel, the communicating hole, the groove, and the hook slot and through hole of the barb on the collection rod.

11. The method according to claim 9, wherein the inner wall of the testing chamber is also provided with a second step located above the first step; a cushion is arranged in the testing chamber; the cushion is located on the second step; and after flowing into the testing chamber, the mixed liquid flows into the cushion first, and then flows from the cushion onto the test element located in the testing chamber.

12. The method according to claim 9, wherein the tail end of the collection rod is tapered; and the sealing sheet is pierced through the tapered tail end of the collection rod.

13. The method according to claim 9, wherein an outer wall of a bottom of the testing chamber is provided with a sealing gasket, the blood collection structure and the testing chamber enter into the pipetting chamber, and sealing is formed between the testing chamber and the pipetting chamber through the sealing gasket.

14. The method according to claim 9, wherein the collection rod is provided with an annular disc and an annular gasket sleeved on the collection rod, and a bottom of the testing chamber forms sealing with the annular disc through the annular gasket.

* * * * *